US007612885B2

(12) United States Patent
Cole et al.

(10) Patent No.: US 7,612,885 B2
(45) Date of Patent: Nov. 3, 2009

(54) SPECTROSCOPY METHOD AND APPARATUS FOR DETECTING LOW CONCENTRATION GASES

(75) Inventors: Barrett E. Cole, Bloomington, MN (US); James Allen Cox, New Brighton, MN (US); Yuandong Gu, Plymouth, MN (US); Rodney H. Thorland, Shoreview, MN (US)

(73) Assignee: Honeywell International Inc, Morristown, NJ (US)

( * ) Notice: Subject to any disclaimer, the term of this patent is extended or adjusted under 35 U.S.C. 154(b) by 166 days.

(21) Appl. No.: 11/615,617

(22) Filed: Dec. 22, 2006

(65) Prior Publication Data

US 2008/0151248 A1    Jun. 26, 2008

(51) Int. Cl.
*G01N 21/00* (2006.01)
(52) U.S. Cl. ..................... 356/437; 356/436
(58) Field of Classification Search .......... 356/432–444
See application file for complete search history.

(56) References Cited

U.S. PATENT DOCUMENTS

| 5,815,277 | A | 9/1998 | Zare et al. ............ 356/440 |
| 5,912,740 | A | 6/1999 | Zare et al. ............ 356/437 |
| 6,084,682 | A | 7/2000 | Zare et al. ............ 356/437 |
| 6,094,267 | A | 7/2000 | Levenson et al. ......... 356/349 |
| 6,233,052 | B1 | 5/2001 | Zare et al. ............ 356/437 |
| 6,377,350 | B1 | 4/2002 | Paldus et al. ............ 356/454 |
| 6,452,680 | B1 | 9/2002 | Paldus et al. ............ 356/436 |
| 6,466,322 | B1 | 10/2002 | Paldus et al. ............ 356/437 |
| 6,532,071 | B2 * | 3/2003 | Zare et al. ............ 356/437 |
| 7,050,170 | B2 | 5/2006 | Chilese et al. ............ 356/437 |
| 7,106,763 | B2 | 9/2006 | Tan et al. ............ 372/9 |
| 7,259,856 | B2 * | 8/2007 | Kachanov et al. .......... 356/437 |
| 7,352,463 | B2 * | 4/2008 | Bounaix ............ 356/437 |
| 2003/0210398 | A1 | 11/2003 | Augustine et al. .......... 356/432 |
| 2004/0107764 | A1 | 6/2004 | Yan ............ 73/23.37 |
| 2004/0194628 | A1 | 10/2004 | Mitra | |
| 2005/0040337 | A1 | 2/2005 | Cox et al. | |
| 2005/0052653 | A1 | 3/2005 | Fidric ............ 356/437 |
| 2005/0062972 | A1 | 3/2005 | Krusen ............ 346/437 |

(Continued)

FOREIGN PATENT DOCUMENTS

EP    1070943    1/2004

(Continued)

*Primary Examiner*—Michael P Stafira
(74) *Attorney, Agent, or Firm*—Kris T. Fredrick

(57) ABSTRACT

The invention is a method and apparatus capable of detecting constituents of a gas at extremely low concentrations comprising providing a medium that is absorbent of at least a first particular gas under a first environmental condition and desorbent of the particular gas under a second environmental condition, exposing the medium to a sample gas for a first period of time under the first environmental condition, during a second period of time after the first period of time, exposing the medium to the second environmental condition to cause the medium to desorb gas into an optical cavity of a cavity ring down spectrometer and introducing electromagnetic radiation into the cavity, during a third period of time after the second period of time, ceasing introduction of the electromagnetic radiation into the cavity and detecting the decay of the electromagnetic radiation in the cavity, and analyzing the decay of the light in the cavity to obtain a spectral analysis of the sample gas.

32 Claims, 4 Drawing Sheets

U.S. PATENT DOCUMENTS

| | | |
|---|---|---|
| 2005/0094158 A1 | 5/2005 | Paldus et al. ............... 356/519 |
| 2005/0122520 A1 | 6/2005 | Yan ............................ 356/437 |
| 2005/0122523 A1 | 6/2005 | Yan ............................ 356/437 |
| 2005/0134836 A1 | 6/2005 | Paldus et al. ................. 356/73 |
| 2005/0254056 A1 | 11/2005 | Kachanov et al. ........... 356/437 |
| 2006/0082778 A1 | 4/2006 | Paldus et al. ............... 356/437 |
| 2006/0083284 A1 | 4/2006 | Paldus et al. ................. 372/97 |
| 2006/0084180 A1 | 4/2006 | Paldus et al. ............... 436/171 |
| 2006/0087655 A1 | 4/2006 | Augustine et al. ........... 356/437 |

FOREIGN PATENT DOCUMENTS

| | | |
|---|---|---|
| EP | 1847825 | 10/2007 |
| WO | WO-2002/004903 | 1/2002 |
| WO | WO 03/098173 | 11/2003 |
| WO | WO-2005/108939 | 11/2005 |

* cited by examiner

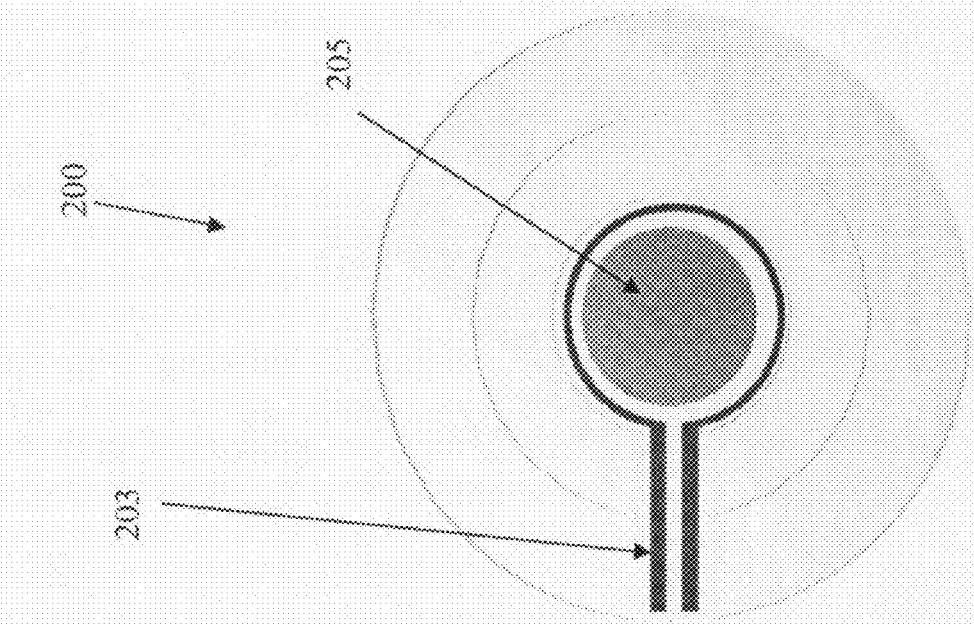
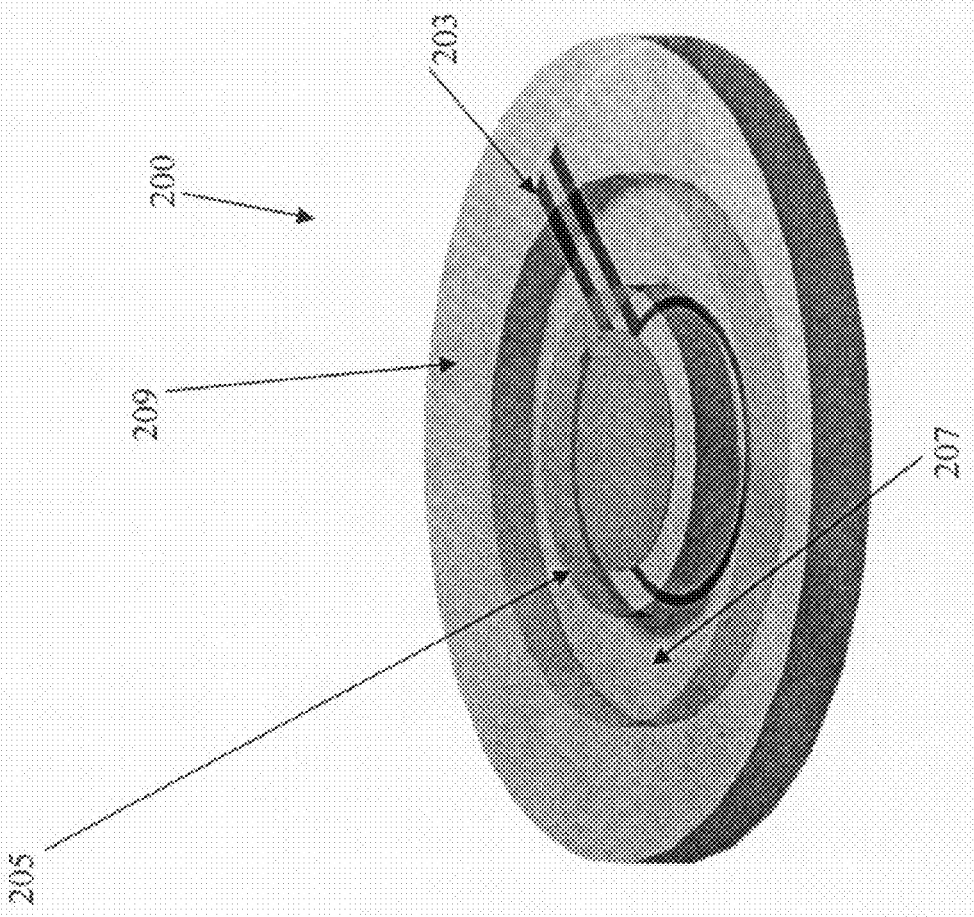

SPECTROSCOPY METHOD AND APPARATUS FOR DETECTING LOW CONCENTRATION GASES

FIELD OF THE INVENTION

The invention pertains to detection and measurement of low concentration gases using spectroscopy techniques.

BACKGROUND OF THE INVENTION

The ability to detect and measure gases at very low concentrations in an environment has many potential commercial and military uses. For instance, it may be desirable to detect poisonous gases in the air in a battlefield or other environment.

A well-known class of techniques for detecting gases is spectroscopy. Spectroscopy is a scientific technique by which electromagnetic radiation, e.g., light, from a given source is segregated into its wavelength components and the relative light power at each wavelength is analyzed to determine the identity or physical properties of the molecules or atoms of the source of that radiation. Particularly, the wavelengths of radiation that are or are not in the spectrum are indicative of the atoms or molecules that are in the source of the radiation. The term "source" is used broadly herein to encompass not only objects that emit radiation, but also objects that merely reflect, transmit, or absorb radiation emitted by another source.

Within these spectra, one can study emission and/or absorption lines, which are the fingerprints of atoms and molecules. For instance, every atomic element has a particular emission and/or absorption spectrum.

There are several different physical phenomena that can cause any particular molecule or atom to have its particular spectral signature. They include electronic, rotational, and vibrational characteristics. The electronic characteristic refers to the spacing of electron orbits of the atoms. The location and spacing of spectral lines is unique for each atom and, therefore, each atom produces a unique emission or absorption spectrum. The electronic characteristic of a source usually is the dominant characteristic producing the signature spectrum, for instance, in the visible wavelengths.

On the other hand, in the near infrared (IR) range (which is roughly 0.75-3.0 microns), midwave IR range (about 3.0-8.0 microns), and longwave IR range (about 8.0-30 microns], the dominant mechanism responsible for spectral absorption bands are not transitions between electron energy levels, but rather transitions between molecular vibrational energy levels. In the far IR range, sometimes referred to as the Terahertz or THz range (about 30-3000 microns), molecular rotational energy levels are the dominant mechanism.

In the THz regime (far IR), there is an even further physical mechanism that affects the spectral absorption bands. Specifically, solid materials exhibit different spectra based on the absorption spectra of the material's crystalline lattice vibrations (so called phonon spectrum). The principle is the same, but the fundamental mechanism for spectral emissions is lattice vibrations rather than molecular vibrations or rotations.

The overall spectral signature of a gas (or any other object) in any given wavelength band may be the result of any one or more of these phenomena. It does not matter for measurement purposes which physical phenomenon is the cause of any particular spectral line.

Even further, continuous spectra (also called thermal spectra) are emitted by any object that radiates heat, i.e., has a temperature above absolute zero. The light (or other electromagnetic radiation) is spread out into a continuous band with every wavelength having some amount of radiation. Accordingly, the magnitude of radiation at a given wavelength or wavelengths may be used to determine the general composition of an object and/or its temperature or density.

Cavity Ring Down Spectroscopy (CRDS) is one particular spectroscopy technique that can measure the presence and/or concentration of gases in an environment by measuring the absorption spectra of the gas.

Generally, in CRDS, electromagnetic radiation, such light from a laser source, is introduced into a cavity containing the gas to be measured. Mirrors are arranged in the cavity so as to cause the light beam to continuously travel in a loop in the cavity. For instance, a cavity employing two mirrors that causes the light to travel back and forth between the two mirrors continuously can be used. Alternately, three mirrors can be positioned in the cavity to cause the light to continuously travel around the cavity in one direction. A typical CRD cavity could provide an effective path length of several kilometers in a very compact design, e.g., 50 centimeters per side. The light in the cavity will dissipate over a certain period of time as a result of primarily two factors, namely, (1) the absorption of the light by the molecules of the gas in the cavity and (2) the inherent losses of the cavity itself. The inherent losses of the cavity include phenomena such as scatter, less than perfect reflectivity of the mirrors, and absorption by the mirrors and other elements in the cavity that the light strikes. If the inherent losses of the cavity are determined, such as by empirical measurement, their effect on the light dissipation time can be subtracted out of any results, thus leaving the dissipation time caused by absorption of the light by the gas in the cavity.

The rate of absorption of the light by the gas is dictated largely by two factors, namely, (1) the cross-section of the particular gas molecule at the wavelength of the light and (2) the path length of the cavity. The cross-section of the gas molecules at the particular wavelengths at which it will be tested should be empirically or otherwise determined and known ahead of time.

If a particular wavelength corresponds to a spectral peak of the gas, then the decay time will be shorter at that wavelength. The decay time is predictive, not simply of the presence of a particular gas (having a spectral peak at the wavelength been tested), but also its concentration.

Thus, given knowledge of the path length of the cavity, the inherent losses of the cavity, and the pre-known cross-section of the gas molecule at the particular wavelength of the light injected into the cavity, then the length of time necessary for light in the cavity to dissipate can be readily converted into a spectral absorption characteristic for the gas in the cavity. Light at more than one wavelength can be introduced into the cavity sequentially in order to obtain a spectral analysis at several wavelength points.

CRDS systems can be used to detect extremely low concentrations of gases in an environment, as low as a few parts per billion. However, there are environments and circumstances (e.g., battlefield poisonous gas detection) in which it would be desirable to detect the presence of particular gases at much lower concentrations, including a few parts per trillion or a few parts per quadrillion.

SUMMARY OF THE INVENTION

The invention is a method and apparatus capable of detecting constituents of a gas at extremely low concentrations comprising providing a medium that is absorbent of at least a first particular gas under a first environmental condition and desorbent of the particular gas under a second environmental condition, exposing the medium to a sample gas for a first period of time under the first environmental condition, during a second period of time after the first period of time, exposing the medium to the second environmental condition to cause the medium to desorb gas into an optical cavity of a cavity ring down spectrometer and introducing electromagnetic radiation into the cavity, during a third period of time after the second period of time, ceasing introduction of the electromagnetic radiation into the cavity and detecting the decay of the electromagnetic radiation in the cavity, and analyzing the decay of the light in the cavity to obtain a spectral analysis of the sample gas.

BRIEF DESCRIPTION OF THE DRAWINGS

FIG. 2A is a partially transparent top perspective view of an exemplary heated mirror assembly in accordance with an embodiment of the present invention.

FIG. 2B is a partially transparent bottom plan view of the exemplary heated mirror assembly of FIG. 2B.

DETAILED DESCRIPTION OF THE INVENTION

Figure 1:
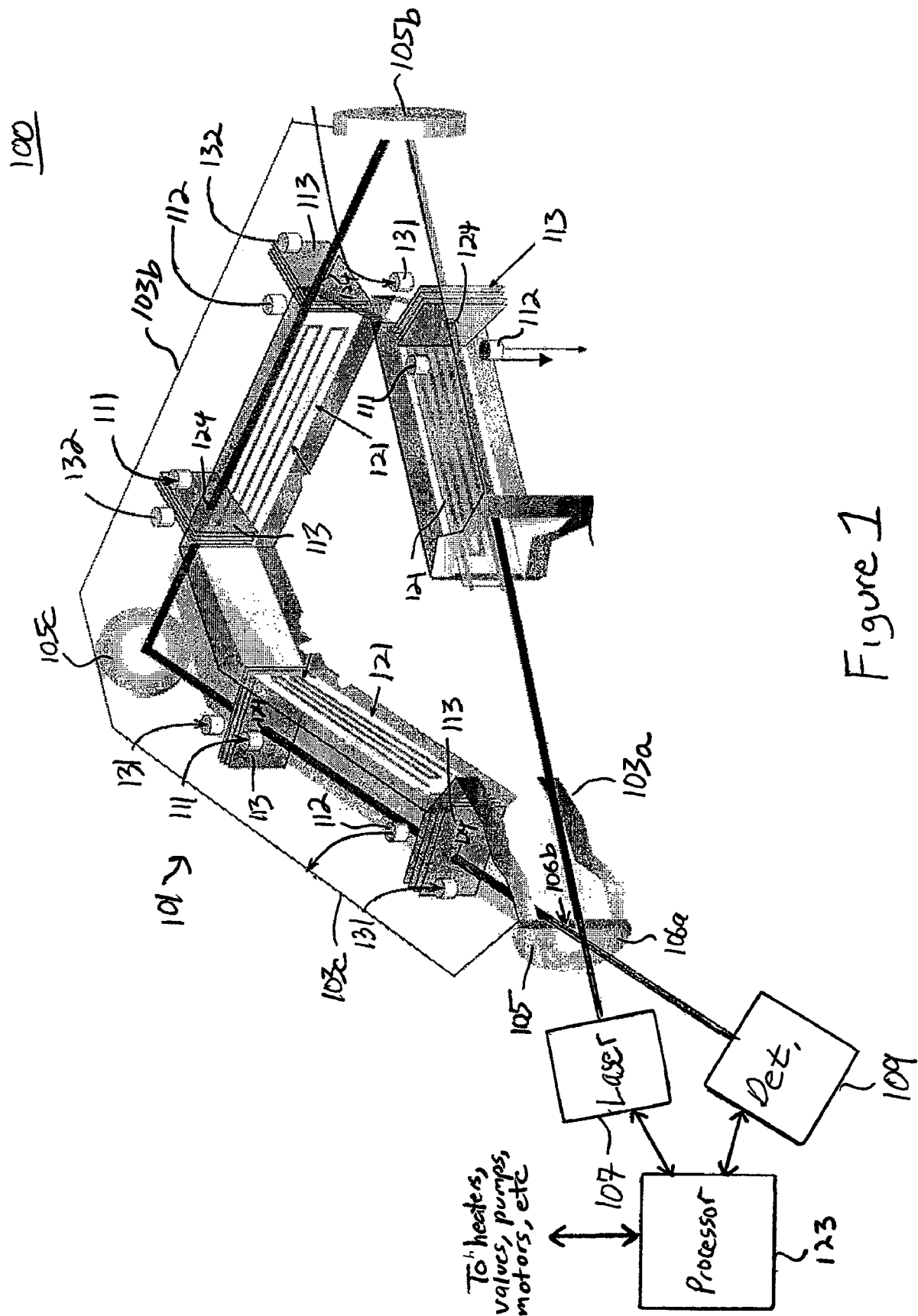
FIG. 1 is a partially transparent perspective diagram of a cavity ring block of a Cavity Ring Down Spectrometer in accordance with one embodiment of the present invention.

FIG. 1 is a partially transparent perspective diagram of a cavity ring down block of a Cavity Ring Down Spectrometer (CRDS) in accordance with one embodiment of the present invention. The CRD block 100 comprises a cavity 101 defined by three linear segments 103a, 103b, 103c forming a triangle. At each corner of the block 100, a mirror 105a, 105b, 105c is positioned at an angle designed to permit a light beam to travel in a continuous path in the cavity. In this particular embodiment, the path is triangular. Light is introduced into the path in the cavity in any reasonable fashion. In the illustrated embodiment, a laser light source 107 directs a beam of light onto the back side of one of the mirrors 105a. Mirror 105a is partially transparent so as to allow a portion of the incident beam to pass through the backside 106a of the mirror and enter the cavity path. The other two mirrors 105b, 105c preferably are as reflective as possible so as to minimize cavity light losses. The partially transparent mirror 105a, of course, also partially transmits therethrough the light incident on it from the front side 106b, thus permitting a detector 109 to detect the amount of light remaining in the cavity at any given instant in time and, particularly, to measure when there is no more light remaining in the cavity.

It should be understood that the above-described cavity is exemplary and that the cavity can be of any design that permits light to be introduced into the cavity, travel around the cavity, and permits direct or indirect measurement of the amount of light in the cavity.

It should also be understood that the term light is used herein broadly to refer to electromagnetic radiation at any wavelength. In fact, many practical embodiments of the invention will employ light in the near to far infrared portion of the electromagnetic spectrum.

The cavity 101 includes one or more gas inlet paths 111 and one or more gas outlet paths 112 for permitting the ingress and egress of the sample gas to be tested. Depending on the specific application of the CRDS system, the inlet and outlet paths may simply be pipes or tubes open at their far ends to the environment of interest. One or more pumps may be employed to help the gas flow into the cavity. In other applications in which the gas to be tested is previously contained, the gas inlet path(s) may be coupled to a chamber containing the gas and the gas outlet valves may be coupled to an empty chamber. Suitable pumps can be employed to pump gas into and out of the CRDS cavity.

In a preferred embodiment of the invention, physical baffles 113 with apertures to permit the light beam to pass through unaffected may be disposed near each of the mirrors, with one baffle/aperture on each side of the mirror in order to protect and isolate the portions of the cavity in which the mirrors 105a, 105b, 105c are contained from the sample gas. The baffle/aperture would have an opening for permitting the light to pass through as it travels around the cavity. The opening does not serve any optical purpose, merely the physical purpose of isolating to the extent possible the mirrors from exposure to the sample gas. Particularly, if the mirrors are exposed to the sample gas, the sample gas may deposit and build up on the mirrors, thereby adversely affecting its reflectivity or other properties, throwing off the measurement accuracy, or even damaging the mirror permanently. Accordingly, depending on the particular application, it may or may not be desirable to take such precautions to prevent the sample gas from contacting or coating the mirrors.

In an even further embodiment of the invention, the mirror of portions of the cavities can be pumped with an inert gas such as helium or argon to help keep the mirror environment clean, as illustrated in FIG. 1 by inert gas inlet and outlet valves 131, 132, respectively, located in the mirror containing portions of the cavity 101.

Another option for preventing the sample gas from depositing on the mirrors is to occasionally heat the mirrors to cause any gases that may have deposited on the mirrors to volatilize or to continually heat the mirrors during the periods of gas exposure to prevent the gas from condensing on the mirrors at all.

FIGS. 2A and 2B are partially transparent top and bottom views illustrating an exemplary heated mirror assembly that can be used in accordance with this aspect of the invention. The mirror 200 may be heated by a suitable heating means, such as a Peltier heater or a thermal resistor 203. In order to minimize the power required to heat the mirrors, it would be desirable to design the mirror to be highly thermally isolated from the rest of the CRDS block. This can be accomplished, for instance, by mounting the optical portion 205 of the mirror on a thin membrane 207 that supports the optical portion 201 of the mirror 200 on the mirror support 209. A thermal resistor 203 or other very small heating element can be placed on the back side of the optical portion of the mirror in order to heat it.

In another embodiment, the entire CRDS block may be heated. However, in embodiments including the pre-concentrators as described previously, it may not be practical to heat the entire block since the temperature of the pre-concentrators must be maintained below the desorption temperature of the expected sample gases most of the time in order for the system to work as intended. Of course, if the entire CRDS block is heated, the pre-concentrators can be separately cooled to maintain them at the desired temperature during pre-concentration.

Note that one or more environmental conditions other than temperature can be used to switch the absorbent material between absorbing and desorbing states. For instance a change from a higher ambient pressure to a lower ambient pressure surrounding the material can achieve the same result. The pressure can be changed using suitable vacuums or pumps.

In accordance with another aspect of the invention, one or more of the mirrors may be movable so as to change the effective length of the cavity. Particularly, in order to obtain the highest measurement sensitivity, it is often desirable to tune the length of the cavity to an integer multiple of the wavelength of the light in the cavity, i.e., to make the cavity resonant. As will be discussed further below, it may be desirable to use tunable lasers to be able to take measurements at different wavelengths in order to detect multiple spectral lines. In such cases, the wavelength of the laser and the length of the cavity could be tuned simultaneously to assure that the cavity length is an integer multiple of the particular wavelength of the light in the cavity.

In one embodiment of the invention, an absorbing media 121, hereinafter referred to as a pre-concentrator, is disposed in the cavity, and particularly, in the portion of the cavity exposed to the sample gas (in those embodiments containing isolation mechanisms such as the aforementioned baffles/apertures 113 between the mirrors and the sample gas). In this embodiment, the laser remains off during a pre-concentration period of the system cycle. During the pre-concentration period, sample gas is pumped into or otherwise caused to enter and remain in the cavity and is absorbed by the pre-concentrator so as to become concentrated in the pre-concentrator media. Then, after a sufficient pre-concentration period, the system enters a measurement period in which (1) the pre-concentration media is quickly heated above the desorption temperature of the gas(es) being tested for to cause it to quickly desorb the gas, (2) the laser 101 is turned on and then off in order to introduce light into the cavity, and (3) the detector 101 is turned on to measure the decay time of the light in the cavity after the laser is turned off. In this way, the measurement is taken of a highly concentrated sample. In some embodiments of the invention, the gas may be permitted to flow through the cavity during the pre-concentration phase and/or measurement phase. In other embodiments, the gas may be admitted into the collection chamber and the collection chamber sealed during the pre-concentration phase.

Merely as an example, if the collection period is one thousand times longer than the measurement period, there should be an approximately 1000 fold increase in gas concentration relative to that of the original, unconcentrated sample gas.

In one preferred embodiment of the invention, an electronic shutter 124 may be disposed in the baffle/aperture. The shutter may be kept closed to even better physically isolate the portions of the cavity containing the mirrors from the portions of the cavity containing the sample gas during the pre-concentration periods (during which the laser is off). This would cause the mirrors to be sealed off from the gas-containing portion of the cavity most of the time. For example, if the pre-concentration phase is set to 1000 ms and the measurement phase is set to 1 ms, this should permit an approximately 1000 fold decrease in the amount of gas that accumulates on the mirrors over a given period of time.

Figure 3:
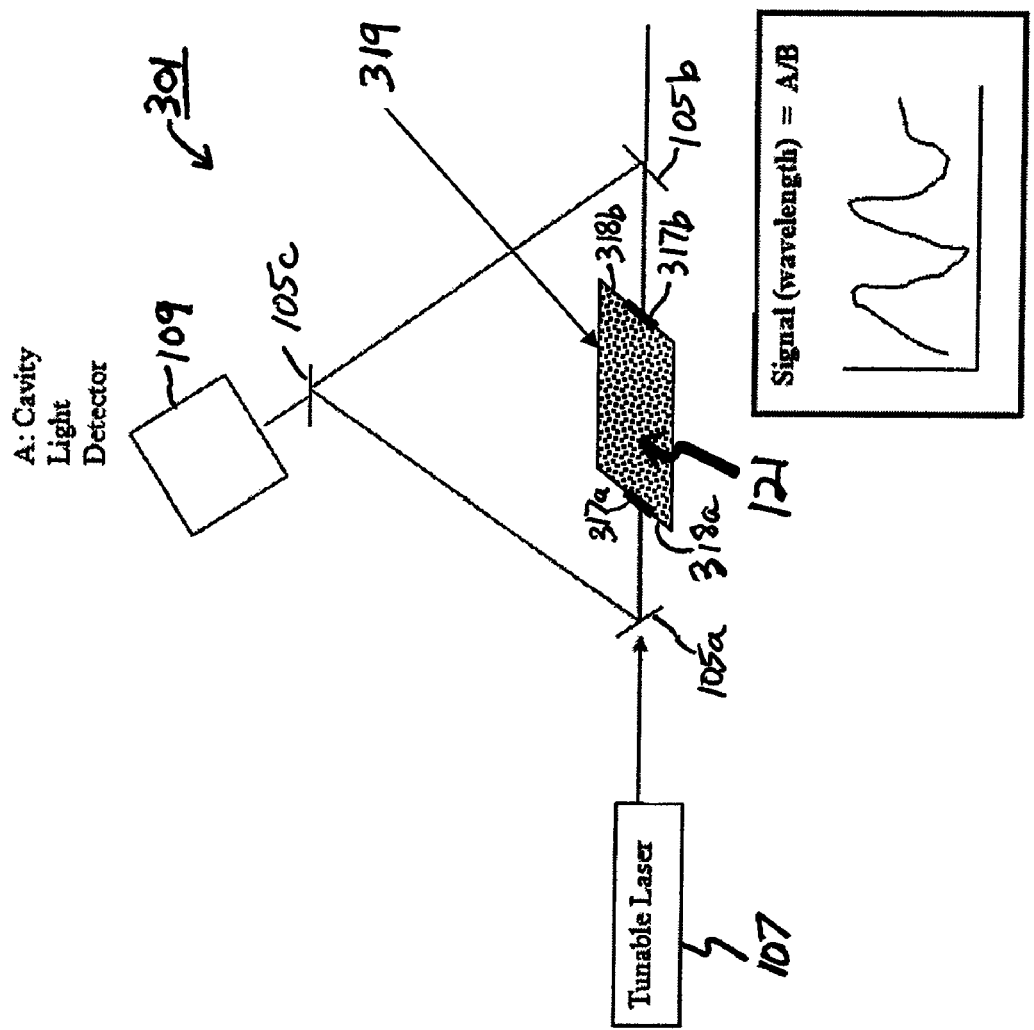
FIG. 3 is a partially transparent perspective diagram of a cavity ring block of a Cavity Ring Down Spectrometer in accordance with a second embodiment of the present invention.

In an alternative embodiment of the invention illustrated schematically in FIG. 3, instead of baffles/apertures 313, Brewster windows may be employed. Brewster windows are optical coupling elements that, when placed at a particular angle to an incident light beam, have essentially zero loss. Brewster windows 317a, 317b could be placed on or formed as part of the two ends 318a, 318b of a completely enclosed chamber 319 that can be used as part of the CRD cavity 301. This type of embodiment may be particularly desirable where highly dangerous gases are being studied. Such a chamber 319 can be completely enclosed and the gas to be tested can be captured in the chamber. The preconcentrator media 121 is disposed in the chamber 319. The chamber 319 can be placed in the CRD assembly for CRDS measurement and then removed and disposed of properly. This would likely increase the safety of the individuals working with the system. It also would have the added benefit of completely isolating the mirrors from the sample gas.

In one embodiment of the invention, the pre-concentrator can be heated up above the desorption temperature of the gas or gases being tested for all at once in order to volatilize all of the gas from the pre-concentrator simultaneously. However, in another embodiment of the invention, it may be possible to attain even more discriminating data by heating up the pre-concentrator slowly so that gases having different volatilization temperatures desorb from the pre-concentrator at different times. Such an embodiment may provide additional desorption temperature information that can be combined with the spectral analysis information to even more accurately predict the composition of the gas in the cavity.

In another embodiment of the invention, the pre-concentrator can be incorporated into the gas inlet path 111 rather than in the cavity itself. For instance, the inlet pipe or hose can be coated with pre-concentrating material and the pre-concentrating material can be heated by before the measurement is taken.

In another embodiment of the invention, the pre-concentrator may also be coupled to a cooling system as well as to a heating system in order to more accurately control its instantaneous temperature.

The pre-concentration media can be any structure or material that can absorb one or more of the gases that the system is intended to measure. In one embodiment of the invention, the pre-concentrator media comprises carbon nano-tubes. For instance, the assignee of the present application, Honeywell International Inc., manufactures carbon nano-tubes that have very broad band absorption characteristics and could be used in applications in which many gases will be tested for. In other embodiments in which only one or a small number of gases will be tested for, it may be more advisable to use a pre-concentrator material that is selectively absorbent of a narrow range of gases (encompassing the gas(es) of interest). The assignee of the present application also manufacturers various zeolites having particular selective absorption characteristics.

Zeolite molecular sieves are crystalline structures that, on a molecular scale, are like sponges. They have a solid framework, defined by large internal cavities where molecules can be adsorbed. These cavities are interconnected by pore openings through which molecules can pass, and because of their crystalline nature, the pores and cavities are all precisely the same size. Depending on the size of the openings, they can adsorb molecules readily, slowly, or not at all, thus functioning as molecular sieves—adsorbing molecules of certain sizes while rejecting larger ones. The ability of these molecular sieves to attract and sort molecules is also affected by the electrical charge or polarity of the molecules being sorted. Synthetic zeolites possess the unique ability to selectively adsorb molecules by size and polarity. Synthetic zeolites can be manufactured to provide a wide range of desired adsorption characteristics or selectivities. Such zeolites could be used in these types of applications.

Another media suitable for use as the pre-concentrator are coated nano-wires.

Specific suitable materials include Honeywell nanoglass marketed by the assignee of the present application, and VOC concentrators, which are just one class of many suitable zeolites. For example, UOP, LLC, an affiliate of the assignee of the present application markets a line of HiSiz adsorbents, which are zeolites that capture and concentrate Volatile Organic Compounds (VOCs) and Hazardous Air Pollutant (HAPs) compounds.

In a simple embodiment of the invention that tests for only one gas and that gas, for example, has one spectral peak that is highly indicative of the presence of that gas, then the system can be employed so as to simply obtain the light decay time at a single wavelength. However, in more complex embodiments in which measurement of light decay time at multiple wavelengths is needed or desired to accurately predict the presence or concentration of a particular gas, the cavity would need to be pumped with light at multiple different wavelengths and the light decay time measured for each wavelength.

This can be accomplished by using a different laser for each different wavelength at which a measurement is to be taken. However, more preferably, a tunable laser can be employed.

As previously noted, if different wavelengths of light are introduced into the cavity, and it will be desirable to place a least one of the mirrors, e.g., mirror 105a, on a movable mount so as to permit an adjustment of the cavity length. Particularly, the highest sensitivity measurements typically are attainable when the cavity length is an integer multiple of the wavelength of the radiation. The mirror be mounted on a track and be moveable under control of a servo-motor or a piezoelectric transducer, for instance.

In one embodiment of the invention, the inherent cavity losses are measured immediately after (or before) each measurement of the sample gas. For instance, this can be accomplished by purging the cavity of gas, turning on the laser, and taking a measurement immediately after taking a measurement of the sample gas.

In another embodiment of the invention, a measurement can be taken of the sample gas at a particular wavelength (which should, of course, correspond to an expected peak of the gas being tested for). Then, immediately after or before that measurement and while the sample gas is still in the chamber, another measurement of decay time can be taken at a wavelength different but very close to the wavelength used for the sample gas test, but which is completely off of that peak. The difference between these two measurements should accurately reflect the amount time of the decay of the first measurement that was a result of absorption by the gas as opposed to the inherent cavity losses.

In practice, maximal sensitivity of measurement is obtained when the losses from absorption by the gas are equal to the inherent cavity losses. Accordingly, steps can be taken in the design of the cavity to make its inherent loss approximately equal to the likely losses due to absorption by the sample gas.

In another embodiment of the invention, it may be desirable to place filtering materials either in the cavity or in the inlet path 111 to filter out from the cavity gases not of interest. These filtering materials could be absorbing materials very much like the pre-concentrators, except that they would be highly selectively absorbent materials that absorb only a particular type or class of gas. This type of embodiment would be particularly useful in situations where a gas to be tested for is likely to be mixed with another gas that is not of interest, but that has spectral peaks equivalent or close to the spectral peaks of the gas(es) that are of interest.

In a preferred embodiment, the filtering material may be heated up occasionally above the volatilization temperature of the collected gas(es) (at times other than during active use of the device for taking measurements) in order to purge the system of these pollutants gases.

In accordance with another embodiment of the invention, such pollutant gases can be prevented from entering the cavity by disposing a selectively permeable material in the inlet path. Particularly, the permeable membranes can selectively permit some gases to flow through and prevent other gases from passing as a function of various criteria. One such criterion is the size of the gas molecule.

A digital processor 123 or the like, such as a general purpose computer, microprocessor, state machine, Application Specific Integrated Circuit (ASIC), digital circuitry, analog circuitry, state machine, etc. is coupled to control the various components of the device in the manner described herein. For example the processor or the like will control the laser(s) to turn it on and off at the appropriate times and also to adjust its output wavelength, control the detector(s) to take the proper measurements at the proper times, control any valves, pumps, vacuums or similar devices for controlling the flow of the sample gases or inert gases, control the motion of any mirrors for adjusting the length of the optical path in the cavity, control any shutters in the baffles, control any or all of the aforementioned heaters and coolers, etc. Furthermore, the same or a different processor also can analyze the collected decay time and other data to determine the inherent cavity loss (and subtract it from the measurements as necessary), determine the absorption spectrum of the sample gas, determine the constituents of the sample gas, determine the concentrations of the constituents of the sample gas, etc.

Figure 4:
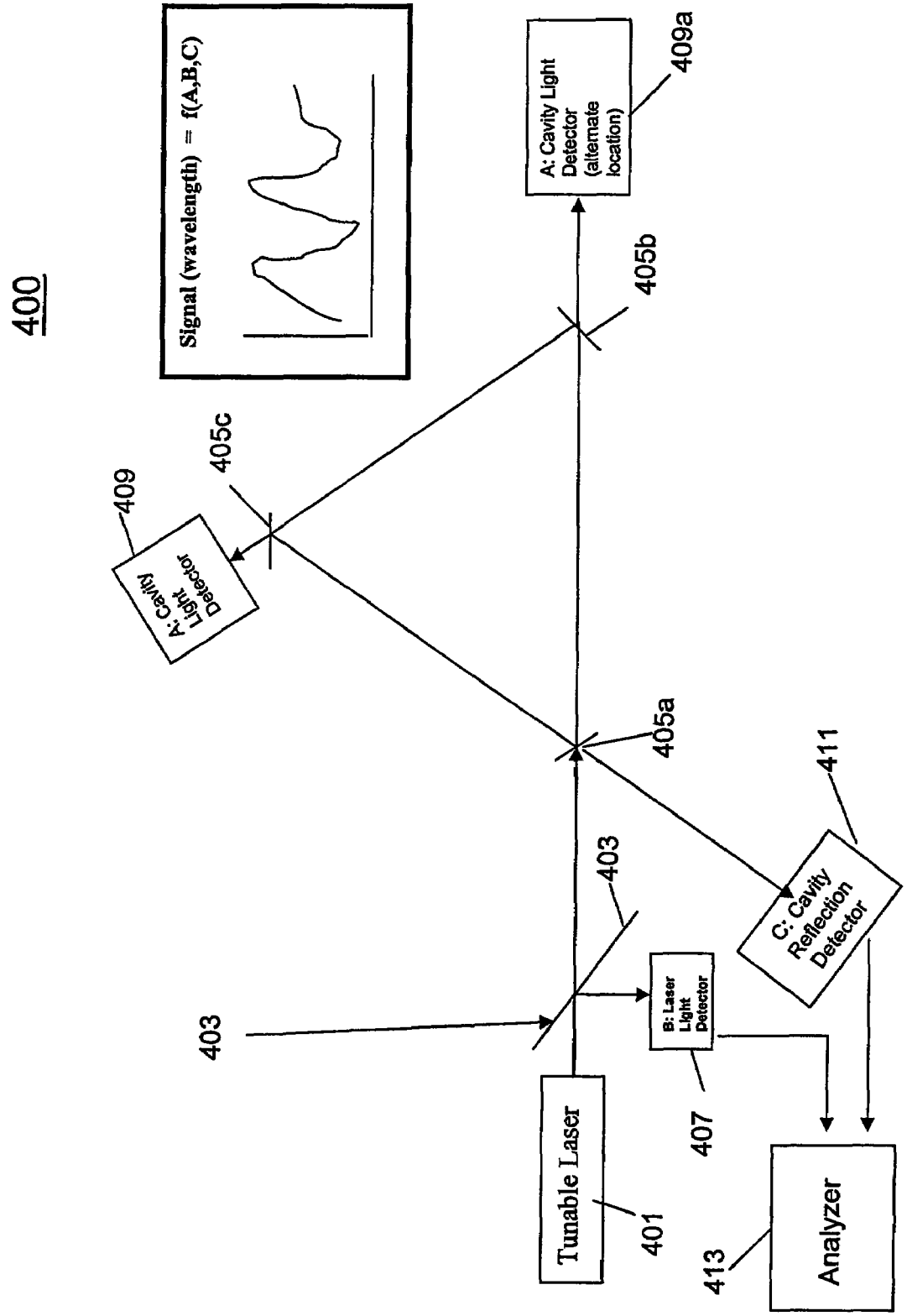
FIG. 4 is a schematic diagram of the measurement portion of a spectrometer in accordance with another embodiment of the present invention.

FIG. 4 is a schematic diagram of another embodiment of the invention. In accordance with the principles of CRDS as described above, the laser is pulsed and the decay time of the light in the cavity is measured after the laser is turned off. In accordance with the embodiment of the invention illustrated in FIG. 3 and described herein below, the spectral characteristics of the sample gas in the cavity alternately can be measured more directly by instead activating the laser during the measurement phase and measuring the ratio between the instantaneous input power into the cavity and the simultaneous instantaneous output power from the cavity.

In this embodiment, a tunable laser 401 provides a light beam to a beam splitter 403. Part of the beam is reflected into a detector 407 that detects the input power of the laser light into the cavity. The remainder of the light beam passes through splitter 403 into the cavity 401 through partially reflective mirror 405a. As in the embodiment of FIG. 1, there are three mirrors 405a, 405b, 405c positioned to cause the light to travel in a continuous loop in the cavity. Another detector 409 detects the power of the light after it has traveled in the cavity, i.e., the output power of the cavity. Detector 409 may be positioned behind any of the mirrors. In FIG. 4, reference numeral 409a indicates an alternate position of the output detector 409. This can be done, as illustrated in FIG. 4, by making any one or more of the cavity mirrors 405a, 405b, 405c partially reflective so the part of beam striking it is passed through and impinges on the detector. The output detector can also be placed behind input mirror 405a (not illustrated) since it already is partially transmissive and partially reflective in order to permit the introduction of the input light from laser 401. Additionally, another detector 411 may be included behind one of the mirrors 405 to measure the reflectivity of the cavity.

As in the CRDS embodiments, the amount of loss between the input power and the output power will be a function of both the absorption of the light by the sample gas in the cavity and the inherent cavity losses.

The inherent cavity losses can be determined in any of the manners previously described. Alternately, inherent cavity loss can be measured by measuring the output power relative to the input power in the absence of a sample gas in the cavity.

The wavelength of the input light can be swept over the desired spectrum in order to obtain the complete absorption spectrum of the sample gas in the cavity. This is to be compared with the point by point technique of the CRDS embodiments of the invention.

The measurements at the different wavelengths should be taken spaced apart in time by a period greater than the response time of the cavity (i.e., the time it takes for the light to completely decay after the laser has been turned off). This is to ensure that no light remains in the cavity from the previous wavelength when the next measurement is taken. This period is on the order of microseconds. Other than that, the laser may be wavelength switched as quickly as desired, limited only by the system's speed capabilities. Accordingly, switching the laser wavelength between wavelengths at a period on the order of milliseconds or even hundreds of microseconds would provide a large safety margin while still permitting measurements of up to or more than 1000 different wavelengths per second.

In this technique, the inherent cavity loss should be separately determined at each different wavelength since the optical properties of the optical components of the cavity may differ at different wavelengths. In addition, in a preferred embodiment of the invention, the cavity length also is adjusted commensurately with the wavelength to maintain the cavity length at a multiple integer of the wavelength of the input light.

In addition, it would be advisable to measure the inherent cavity loss intermittently since the optical characteristics of the optical components of the cavity might change over time.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A spectrometer apparatus comprising:
   a cavity comprising at least two mirrors arranged to provide a continuous light path in said cavity;
   a source for providing electromagnetic radiation into said optical cavity;
   a detector for monitoring the amount of radiation in said cavity and generating a first detection signal based thereon;
   an absorbent medium in fluid communication with said cavity, said medium being absorbent of at least a first particular gas under a first environmental condition and being desorbent of said particular gas under a second environmental condition;
   a means for controlling the environment of said medium between the first environmental condition and the second environmental condition;
   a processor adapted to control said apparatus to (a) control an environment of said medium to expose said medium to a sample gas while under the first environmental condition, (b) subsequently switch said environment to said second environmental condition to cause said medium to desorb, (c) cause said source to provide electromagnetic radiation into said cavity during or after said medium desorbs, (d) subsequently turn off said source, and (e) subsequently measure the decay of the electromagnetic radiation in the cavity during the third period of time.

2. The apparatus of claim 1 wherein said processor is adapted to control said apparatus to expose said medium to the sample gas while under the first environmental condition for a first period of time and, at the end of the first period of time, to switch to said second environmental condition to cause said medium to desorb during a second period of time, turn on said source during said second period of time, turn off said source off at the beginning of a third period of time following said second period of time, and measure the decay of the electromagnetic radiation in the cavity during the third period of time.

3. The apparatus of claim 1 wherein said first environmental condition comprises a first temperature and said second environmental condition comprises a second temperature and wherein said means for controlling comprises a heater for heating said material.

4. The apparatus of claim 3 wherein said means for controlling further comprises a cooling unit for cooling said material.

5. The apparatus of claim 1 wherein said first environmental condition comprises a first pressure and said second environmental condition comprises a second pressure and wherein said means for controlling comprises a pump for applying negative or positive pressure around said medium.

6. The apparatus of claim 1 wherein said medium comprises at least one of carbon nano tubes and a zeolyte.

7. The apparatus of claim 1 further comprising a heater coupled to heat said mirrors.

8. The apparatus of claim 1 wherein said source can provide electromagnetic radiation into said cavity at any one of multiple wavelengths and wherein at least one of said mirrors is movable and wherein said processor is further adapted to move said mirror to cause an optical length of said cavity to be equal to an integer multiple of said wavelength of said electromagnetic radiation.

9. The apparatus of claim 1 wherein said processor is further adapted to analyze the length of time for said electromagnetic radiation in said cavity to decay to obtain a spectroscopic analysis of said sample gas.

10. The apparatus of claim 1 wherein said processor is further adapted to analyze the length of time for said electromagnetic radiation in said cavity to decay and determine at least one of the identity of a constituent of said sample gas and a concentration of said constituent in said sample gas.

11. The apparatus of claim 1 wherein said cavity comprises at least one first portion and at least one second portion and a path for permitting said sample gas to flow over said medium wherein said path comprises at least one inlet path for admitting the said sample gas into said cavity and at least one outlet path for evacuating said sample gas from said cavity, said inlet and outlet paths being disposed in said at least one first portion of said cavity, and said mirrors being disposed in said at least one second portion of said cavity, said apparatus further comprising a plurality of baffles disposed in said cavity and positioned to separate said mirrors from said portions of said cavity containing said inlet and outlet paths.

12. The apparatus of claim 11 wherein each of said baffles include an aperture for permitting said electromagnetic radiation to pass through said aperture unobstructed, and a shutter in each said aperture, said shutter being controlled to close said aperture during said first period of time and to open said shutter during said second period of time.

13. The apparatus of claim 1 wherein cavity comprises at least one first portion and at least one second portion, said mirrors being disposed in said at least one second portion of said cavity and said sample gas being disposed in said at least one first portion of said cavity, said apparatus further comprising a plurality of Brewster windows disposed in said cavity and positioned to separate said mirrors from said portions of said cavity containing said inlet and outlet paths.

14. The apparatus of claim 13 wherein said at least one first portion of said cavity is fluidly sealed from said second portion of said cavity and said first portion has said Brewster windows disposed thereon.

15. The apparatus of claim 14 wherein said at least one first portion of said cavity is modular.

16. A method of detecting constituents of a gas comprising:
  a. providing a medium that is absorbent of at least a first particular gas under a first environmental condition and desorbent of said particular gas under a second environmental condition;
  b. exposing said medium to a sample gas for a first period of time under the first environmental condition;
  c. during a second period of time after said first period of time, exposing said medium to said second environmental condition to cause said medium to desorb gas into an optical cavity of a cavity ring down spectrometer and providing electromagnetic radiation into said cavity;
  d. during a third period of time after said second period of time, ceasing provision of said electromagnetic radiation into said cavity and detecting the decay of said electromagnetic radiation in said cavity; and
  e. analyzing the decay of said light in said cavity to obtain a spectral analysis of said sample gas.

17. The method of claim 16 wherein said first and second environmental conditions are different temperatures.

18. The method of claim 16 wherein steps b, c, and d are repeated for a plurality of different wavelengths of electromagnetic radiation.

19. The method of claim 18 further comprising:
  adjusting the optical length of said cavity as a function of said wavelength of said electromagnetic radiation so that said cavity length is an integer multiple of a wavelength of said electromagnetic radiation.

20. The method of claim 18 further comprising:
  analyze the length of time for said electromagnetic radiation in said cavity to decay at said multiple wavelengths to obtain a spectroscopic analysis of said sample gas.

21. The method of claim 16 further comprising:
  e. during a fourth period of time after said third period of time, exposing said medium to a third environmental condition to cause said medium to further desorb gas into said optical cavity and introducing electromagnetic radiation into said cavity; and
  f. during a fifth period of time after said forth period of time, ceasing introduction of said electromagnetic radiation into said cavity and detecting the decay of said electromagnetic radiation in said cavity;
  whereby different constituents of said sample gas may desorb from said medium during said second period of time and said fourth period of time such that the particular environmental condition under which said decay time was measured may provide an additional degree of data as to the identity of constituents of said sample gas based on volatilization environmental condition.

22. A method of detecting a constituent of the gas comprising:
  a. providing a resonant optical cavity having at least one coupler for permitting electromagnetic radiation from a source into said cavity and permitting electromagnetic radiation to escape from said cavity;
  b. providing an absorbent medium in fluid communication with said cavity, said medium being absorbent of at least a first particular gas under a first environmental condition and being desorbent of said particular gas under a second environmental condition;
  c. introducing a sample gas into said cavity, sufficient to contact and absorb onto the medium under the first environmental condition;
  d. exposing said medium to the second environmental condition to cause said medium to desorb at least a portion of the sample gas;
  e. pumping said cavity with electromagnetic radiation for a first period of time;
  f. detecting an intensity of said electromagnetic radiation pumped into said cavity;
  g. simultaneously with step d f, detecting an intensity of electromagnetic radiation escaping said cavity; and
  h. determining a difference between said intensity of radiation pumped into the cavity and said intensity of electromagnetic radiation escaping from the cavity to derive an absorption characteristic of said sample gas.

23. The method of claim 22 further comprising:
  i. determining at least one constituent of said sample gas based on said absorption characteristic of said sample gas.

24. The method of claim 22 wherein steps e, f, g, and h are repeated in connection with electromagnetic radiation at a plurality of different wavelengths.

25. The method of claim 24 further comprising:
  j. determining at least one constituent of said sample gas based on said absorption characteristic.

26. A cavity ring-down spectrometer comprising:
  a resonant cavity comprising at least two mirrors;
  a source for providing electromagnetic radiation into said optical cavity;
  a detector for monitoring the amount of radiation in said cavity and generating a first detection signal based thereon;
  a path for admitting a sample gas to flow over said medium and in said cavity;
  a processor adapted to control said cavity ring-down spectrometer to expose said medium to the sample gas while under the first environmental condition for a first period of time and, at the end of the first period of time, to switch to said second environmental condition to cause said medium to desorb during a second period of time after said first period of time, turn on said source during said second period of time, turning said source off at the beginning of a third period of time following said second period of time, and measuring the decay of the electromagnetic radiation in the cavity during the third period of time; and
  a heater coupled to at least one of said mirrors to locally heat at the least a reflecting surface thereof.

27. The cavity ring down spectrometer of claim 26 wherein said heater is adapted to teach said mirror above a volatilization temperature of expected constituents in said sample gas.

28. The cavity ring down spectrometer of claim 26 wherein said heater comprises a Peltier heater.

29. The cavity ring down spectrometer of claim 26 wherein said heater comprises a thermal resistor.

30. The cavity ring down spectrometer of claim 26 wherein said mirror comprises:
   an optical portion including said reflective surface and an opposing surface;
   a supporting base; and
   a thin membrane coupling said optical portion to said supporting base;
   wherein said heater is disposed on said optical portion.

31. The cavity ring down spectrometer of claim 30 wherein said heater is disposed on said opposing surface of said optical portion.

32. The cavity ring down spectrometer of claim 31 wherein said heater comprises a thermal resistor.

* * * * *